(12) United States Patent
Trupke et al.

(10) Patent No.: US 9,482,625 B2
(45) Date of Patent: *Nov. 1, 2016

(54) METHOD AND SYSTEM FOR TESTING INDIRECT BANDGAP SEMICONDUCTOR DEVICES USING LUMINESCENCE IMAGING

(71) Applicant: BT Imaging Pty Ltd, Redfern, New South Wales (AU)

(72) Inventors: Thorsten Trupke, Coogee (AU); Robert Andrew Bardos, Bronte (AU)

(73) Assignee: BT IMAGING PTY LTD, Sydney (AU)

( * ) Notice: Subject to any disclaimer, the term of this patent is extended or adjusted under 35 U.S.C. 154(b) by 239 days.

This patent is subject to a terminal disclaimer.

(21) Appl. No.: 14/206,225

(22) Filed: Mar. 12, 2014

(65) Prior Publication Data

US 2014/0191776 A1    Jul. 10, 2014

Related U.S. Application Data

(63) Continuation of application No. 12/299,759, filed as application No. PCT/AU2007/000595 on May 4, 2007, now Pat. No. 8,710,860.

(30) Foreign Application Priority Data

May 5, 2006    (AU) ................ 2006902366

(51) Int. Cl.
    *G01N 21/95*    (2006.01)
    *G01N 21/64*    (2006.01)
    (Continued)

(52) U.S. Cl.
    CPC .......... *G01N 21/9501* (2013.01); *G01N 21/64* (2013.01); *G01N 21/6489* (2013.01); *G01N 21/66* (2013.01); *G01N 21/956* (2013.01); *H01L 31/022425* (2013.01)

(58) Field of Classification Search
    CPC ... G01N 21/9501; G01N 21/66; G01N 21/64
    USPC .................................... 324/761.01
    See application file for complete search history.

(56) References Cited

U.S. PATENT DOCUMENTS

5,006,717 A    4/1991    Tsutsu et al.
6,420,705 B2   7/2002    Chou et al.
(Continued)

FOREIGN PATENT DOCUMENTS

CN    1620601 A    5/2005
DE    19914115     4/1999
(Continued)

OTHER PUBLICATIONS

International Search Report for PCT/AU2007/000595 dated Jul. 23, 2007.
(Continued)

*Primary Examiner* — Thomas F Valone
(74) *Attorney, Agent, or Firm* — Mattingly & Malur, PC

(57) ABSTRACT

Embodiments of methods and systems for identifying or determining spatially resolved properties in indirect bandgap semiconductor devices such as solar cells are described. In one embodiment, spatially resolved properties of an indirect bandgap semiconductor device are determined by externally exciting the indirect bandgap semiconductor device to cause the indirect bandgap semiconductor device to emit luminescence (110), capturing images of luminescence emitted from the indirect bandgap semiconductor device in response to the external excitation (120), and determining spatially resolved properties of the indirect bandgap semiconductor device based on a comparison of relative intensities of regions in one or more of the luminescence images (130).

16 Claims, 8 Drawing Sheets

(51) Int. Cl.
  *G01N 21/66* (2006.01)
  *G01N 21/956* (2006.01)
  *H01L 31/0224* (2006.01)

(56) References Cited

U.S. PATENT DOCUMENTS

| | | | | |
|---|---|---|---|---|
| 8,710,860 | B2* | 4/2014 | Trupke | G01N 21/6489 324/761.01 |
| 2002/0045283 | A1 | 4/2002 | Hasegawa et al. | |
| 2004/0092042 | A1 | 5/2004 | Higgs | |
| 2005/0196882 | A1 | 9/2005 | Steeples | |
| 2005/0252545 | A1 | 11/2005 | Nowlan et al. | |
| 2007/0048884 | A1 | 3/2007 | Nagel | |
| 2008/0103279 | A1* | 5/2008 | Heun | C08G 61/10 528/8 |
| 2011/0025839 | A1 | 2/2011 | Trupke et al. | |
| 2012/0181452 | A1 | 7/2012 | Trupke | |

FOREIGN PATENT DOCUMENTS

| | | |
|---|---|---|
| DE | 10 2005 040 010 A1 | 3/2007 |
| EP | 0 985 924 | 3/2000 |
| EP | 1 416 288 | 5/2004 |
| JP | 9-27526 A | 1/1997 |
| JP | 2002-83852 A | 3/2002 |
| JP | 2007-59907 A | 3/2007 |
| WO | 98/11425 A1 | 3/1998 |

OTHER PUBLICATIONS

International Preliminary Report on Patentability for PCT/AU2007/000595 dated Aug. 11, 2008.

Kaji et al., "Characterization of Polycrystalline Silicon Solar Cells by Electroluminescence," 15th International Photovoltaic Science & Engineering Conference (PVSEC-15), 2005, pp. 153-154.

R.A. Bardos et al., "Comparison of N and P Type Ribbon Grown Multi-Crystalline Silicon Wafers Using Photoluminescence Imaging," Conference Record of the 2006 IEEE 4th World Conference on Photovoltaic Energy Conversion, IEEE, PI, May 1, 2006, pp. 1203-1206.

F. W. Chen et al., "Characterization of PECVD Silicon Nitride Passivation with Photoluminescence Imaging," Conference Record of the 2006 IEEE 4th World Conference on Photovoltaic Energy Conversion, IEEE, PI, May 1, 2006, pp. 1372-1375.

M. A. Ordaz et al., "Machine Vision for Solar Cell Characterization," Proceedings of the SPIE: Machine Vision Applications in Industrial Inspection VII, [Online], vol. 3966, Jun. 5, 2003, pp. 238-248, http://spiedl.aip.org/getpdf/servlet/GetPDFServlet?filetype=pdf&id=PSISDG003966000001000238000001&IDTYPE=cvips&prog=normal.

Y. Takahashi et al., "Luminoscopy-Novel Tool for the Diagnosis of Crystalline Silicon Solar Cells and Modules Utilizing Electroluminescence," Conference Record of the 2006 IEEE 4th World Conference on Photovoltaic Energy Conversion, IEEE, PI, May 1, 2006, pp. 924-927.

T. Trupke et al., "Fast Photoluminescence Imaging of Silicon Wafers," Conference Record of the 2006 IEEE 4th World Conference on Photovoltaic Energy Conversion, IEEE, PI, May 1, 2006, pp. 928-931.

Supplementary Search Report dated Apr. 14, 2009 for corresponding European application 07718842.3.

N. Nango et al., Journal of Applied Physics, "An optical study on dislocation clusters in a slowly pulled silicon crystal", Dec. 1, 1999, vol. 86, No. 11, pp. 6000-6004.

Direct and indirect band gaps, Wikipedia, p. 1, http://en.wikipedia.org/wiki/Direct_and_indirect_band_gaps.

Yoshikawa, Defect characterization of Si-doped GaN films by a scanning near-field optical microscope-induced photoluminescence, App. Phys. Lett., 88, 16905, 2006, p. 1-3.

* cited by examiner

METHOD AND SYSTEM FOR TESTING INDIRECT BANDGAP SEMICONDUCTOR DEVICES USING LUMINESCENCE IMAGING

RELATED APPLICATION

This application is a continuation of U.S. patent application Ser. No. 12/299,759, filed Mar. 6, 2009, which is a 371 of International Application No. PCT/AU2007/000595, filed May 4, 2007, which claims priority to Australian Provisional Patent Application No. 2006902366, filed May 5, 2006. The entire disclosures of these applications are incorporated herein by reference.

TECHNICAL FIELD

The present invention relates generally to semiconductor testing using luminescence imaging and more particularly to testing of indirect bandgap semiconductor devices such as silicon solar cells.

BACKGROUND

Production of a solar cell begins with a bare semiconductor wafer such as a silicon wafer. During production, a metal pattern or grid is applied to the wafer, typically by means of screen printing or a buried contact process. The purpose of the metal pattern or grid is to collect electric current generated in response to excitation of the semiconductor structure of the solar cell by means of an external source of illumination. The metal grid typically comprises multiple fingers that are electrically connected to one or more bus bars.

For reasons of efficiency, on the one hand, it is desirable to maximize the light collection area of a solar cell. This dictates that the fingers should be thin, narrow and widely spaced to reduce shading of the light collection area. Also for reasons of efficiency, on the other hand, it is desirable that the metal fingers transfer electric current with minimal electrical losses. This dictates that the metal fingers should be thick, wide and closely spaced to minimize resistive losses. A large component of solar cell design is thus to achieve a good compromise between these opposing requirements.

Photovoltaic solar cell manufacturing is generally characterized by significant rejection rates of devices that fail to meet required specifications for efficiency and conventional testing methods are generally unable to determine the reasons for solar cells that exhibit poor efficiency.

Regions of a good photovoltaic device are laterally connected in parallel via low series resistance. One specific mode of photovoltaic device failure is that regions in a photovoltaic device become electrically isolated from or poorly connected to other regions in the photovoltaic device. For example, metal fingers break during manufacturing of solar cells, particularly during screen printing of optimal designs that are characterized by very thin fingers. In that case electrical current generated in the immediate vicinity of broken fingers cannot be effectively collected, which results in a loss in efficiency of the solar cell. Another failure mode results from a high contact resistance or specific areas within a solar cell with enhanced contact resistance. Current flow from the bulk of the semiconductor to the metal contacts causes a voltage drop that is determined by the contact resistance. Locally enhanced contact resistances reduce the efficiency of solar cells. Various potential sources of such locally enhanced contact resistances exist in industrially manufactured solar cells.

A need thus exists for methods and systems that enable identification of poorly connected or electrically isolated regions in indirect bandgap semiconductor devices. A need also exists for methods and systems that enable identification of broken metal fingers, bus bars and connections between fingers and bus bars in solar cells, which are a common problem occurring in industrial solar cells.

SUMMARY

Aspects of the present invention relate to methods and systems for identifying or determining spatially resolved properties of indirect bandgap semiconductor devices.

A first aspect of the present invention provides a method for determining spatially resolved properties of an indirect bandgap semiconductor device. The method comprises the steps of externally exciting the indirect bandgap semiconductor device to cause the indirect bandgap semiconductor device to emit luminescence, capturing images of luminescence emitted from the indirect bandgap semiconductor device in response to the external excitation, and determining spatially resolved properties of the indirect bandgap semiconductor device based on a comparison of relative intensities of regions in two or more of the luminescence images.

The step of determining spatially resolved properties may comprise spatially resolving electrically isolated or poorly connected regions in the indirect bandgap semiconductor device.

The step of determining spatially resolved properties may comprise comparing a ratio of intensities between different regions in one of the luminescence images with a ratio of intensities between corresponding regions in at least one other of the luminescence images.

The step of determining spatially resolved properties may comprise comparing relative intensities of regions in at least two luminescence images, which may be selected from the group of luminescence images consisting of: an electroluminescence image generated by exciting the indirect bandgap semiconductor device with an electrical signal; a photoluminescence image generated by exciting the indirect bandgap semiconductor device with incident light suitable for inducing photoluminescence whilst contact terminals of the indirect bandgap semiconductor device are maintained in an open circuit state; and a photoluminescence image generated by exciting the indirect bandgap semiconductor device with incident light suitable for inducing photoluminescence and simultaneously varying a voltage level across contact terminals of the indirect bandgap semiconductor device relative to an open circuit value.

In one embodiment, the step of externally exciting the indirect bandgap semiconductor device may comprise at least one of the following steps: illuminating the indirect bandgap semiconductor device with light suitable for inducing photoluminescence in the indirect bandgap semiconductor device; and applying an electrical signal to contact terminals of the indirect bandgap semiconductor device to induce electroluminescence in the indirect bandgap semiconductor device. Spatially resolved properties may be determined by comparing relative intensities of regions in a photoluminescence image and an electroluminescence image. Electrically isolated or poorly connected regions may correspond to regions of lower intensity relative to other regions in the electroluminescence image with no corresponding regions of varied intensity relative to other regions in the photoluminescence image.

In one embodiment, the step of externally exciting the indirect bandgap semiconductor device may comprise illuminating the indirect bandgap semiconductor device with light suitable for inducing photoluminescence in the indirect bandgap semiconductor device and the method may comprise the further step of simultaneously varying a voltage across contact terminals of the indirect gap semiconductor device relative to an open circuit value. Spatially resolved properties may be determined by comparing intensities of corresponding regions in at least one photoluminescence image without varying a voltage across contact terminals of the indirect gap semiconductor device relative to an open circuit value and at least one photoluminescence image with varying a voltage across contact terminals of said indirect gap semiconductor device relative to an open circuit value. The step of simultaneously varying a voltage across contact terminals of the indirect gap semiconductor device relative to an open circuit value may comprise a step selected from: applying an external bias across contact terminals of the indirect gap semiconductor device; applying a load across contact terminals of the indirect gap semiconductor device; applying a short circuit across contact terminals of said indirect gap semiconductor device; applying a voltage across contact terminals of the indirect gap semiconductor device; injecting current into contact terminals of the indirect gap semiconductor device; and extracting current from contact terminals of the indirect gap semiconductor device. The step of simultaneously varying a voltage across contact terminals of the indirect gap semiconductor device relative to an open circuit value may comprise reducing the voltage across the contact terminals relative to an open circuit value. Electrically isolated or poorly connected regions may correspond to regions of higher intensity relative to other regions in the photoluminescence image having reduced voltage across the contact terminals with no corresponding regions of varied intensity relative to other regions in the photoluminescence image having an open circuit voltage value across the contact terminals.

In one embodiment, the step of externally exciting the indirect bandgap semiconductor device may comprise electrically exciting the indirect bandgap semiconductor device to emit electroluminescence by applying at least one electrical excitation signal to contact terminals of the indirect bandgap semiconductor device. The step of determining spatially resolved properties may comprise comparing intensities of corresponding regions in at least two electroluminescence images, each of the electroluminescence images corresponding to a different level of electrical excitation signal. Electrically isolated or poorly connected regions may correspond to regions of lower intensity relative to other regions in a first electroluminescence image produced with a first level of electrical excitation signal not to regions of lower intensity relative to other regions in a second electroluminescence image produced with a second level of electrical excitation signal, wherein the first level of electrical excitation signal is higher than the second level of electrical excitation signal.

In one embodiment, the step of externally exciting the indirect bandgap semiconductor device may comprise the steps of: applying an electrical signal to contact terminals of the indirect bandgap semiconductor device to induce electroluminescence in the indirect bandgap semiconductor device; and illuminating the indirect bandgap semiconductor device with light suitable for inducing photoluminescence in the indirect bandgap semiconductor device and simultaneously varying a voltage level across contact terminals of the indirect bandgap semiconductor device relative to an open circuit value. The step of determining spatially resolved properties may comprise comparing intensities of corresponding regions in at least one electroluminescence image and at least one photoluminescence image with varying a voltage across contact terminals of the indirect gap semiconductor device relative to an open circuit value. The step of simultaneously varying a voltage across contact terminals of the indirect gap semiconductor device relative to an open circuit value may comprise a step selected from the group of steps consisting of: applying an external bias across contact terminals of the indirect gap semiconductor device; applying a load across contact terminals of the indirect gap semiconductor device; applying a short circuit across contact terminals of the indirect gap semiconductor device; applying a voltage across contact terminals of the indirect gap semiconductor device; injecting current into contact terminals of the indirect gap semiconductor device; and extracting current from contact terminals of the indirect gap semiconductor device. The step of simultaneously varying a voltage across contact terminals of the indirect gap semiconductor device relative to an open circuit value may comprise reducing the voltage across the contact terminals relative to an open circuit value. The electrically isolated or poorly connected regions may correspond to regions of lower intensity relative to other regions in the electroluminescence image and regions of higher intensity relative to other regions in the photoluminescence image with reduced voltage across the contact terminals.

Another aspect of the present invention provides a method for identifying electrically isolated or poorly connected regions in a solar cell, the solar cell comprising a portion of indirect bandgap semiconductor wafer having at least one metal pattern disposed on a surface thereof. The method comprises the steps of exciting the solar cell to emit luminescence, capturing at least one image of the emitted luminescence, and processing the at least one luminescence image to identify breaks in the metal pattern based on a comparison of intensities of regions in the at least one luminescent image. The metal pattern may comprise a grid comprising a plurality of parallel fingers electrically connected to at least one bus bar, and wherein the electrically isolated regions comprise a break in one or more of items selected from the group consisting of: a finger; a bus bar; and a connection between a finger and a bus bar.

In one embodiment, the solar cell may be excited with an electrical signal to induce emission of electroluminescence. A broken finger may be identified based on detection of a region of relatively lower intensity in the electroluminescence image. The region of relatively lower intensity may comprise an elongated region proximate to a portion of a finger.

In one embodiment, the solar cell may be excited to emit luminescence by illuminating the solar cell with incident light suitable for inducing photoluminescence and simultaneously varying a voltage level across contact terminals of the solar cell relative to an open circuit value. Simultaneously varying a voltage level across contact terminals of the solar cell may comprise: applying an external bias across contact terminals of the solar cell; applying a load across contact terminals of the solar cell; applying a short circuit across contact terminals of the solar cell; applying a voltage across contact terminals of the solar cell; injecting current into contact terminals of the solar cell; or extracting current from contact terminals of the solar cell. A broken finger may be identified based on detection of a region of relatively higher intensity. The region of relatively higher intensity may comprise an elongated region proximate to a portion of a finger.

The step of processing at least one luminescence image may comprise identifying breaks in the metal pattern based on a comparison of relative intensities of regions in at least two luminescent images. The at least two luminescence images may comprise luminescence images selected from the group of luminescence images consisting of: an electroluminescence image generated by exciting the solar cell with an electrical signal; a photoluminescence image generated by exciting the solar cell with incident light suitable for inducing photoluminescence whilst contact terminals of the solar cell are maintained in an open circuit state; and a photoluminescence image generated by exciting the solar cell with incident light suitable for inducing photoluminescence and simultaneously varying a voltage level across contact terminals of the solar cell relative to an open circuit value. The processing step may comprise comparing a ratio of intensities between different regions in one of the luminescence images with a ratio of intensities between corresponding regions in at least one other of the luminescence images.

Another aspect of the present invention provides an apparatus for determining spatially resolved properties of an indirect bandgap semiconductor device. The apparatus comprises excitation means for exciting the indirect bandgap semiconductor device to emit luminescence, image capture means for capturing images of luminescence emitted by the indirect bandgap semiconductor device, and processing means for processing the luminescence images to determine spatially resolved properties of the indirect bandgap semiconductor device based on a comparison of relative intensities of regions in two or more of the luminescence images.

Another aspect of the present invention provides an apparatus for identifying electrically isolated or poorly connected regions in a solar cell, the solar cell comprising a portion of indirect bandgap semiconductor wafer having at least one metal pattern disposed on a surface thereof. The apparatus comprises excitation means for exciting the solar cell to emit luminescence, image capture means for capturing at least one image of the emitted luminescence, and processing means for processing the at least one luminescence image to identify breaks in the metal pattern based on a comparison of intensities of regions in the at least one luminescent image.

BRIEF DESCRIPTION OF THE DRAWINGS

A small number of embodiments are described hereinafter, by way of example only, with reference to the accompanying drawings in which.

DETAILED DESCRIPTION

Embodiments of methods and systems are described hereinafter for electroluminescence and photoluminescence imaging of indirect bandgap semiconductor devices. Although certain of the embodiments are described with specific reference to solar cells, it is not intended that the present invention be limited to such devices as the principles of the present invention have general applicability to photovoltaic devices and/or semiconductor devices and structures, which may either be fully or partially processed.

In the context of the present specification, references to electrically isolated or poorly connected regions are intended to include partially electrically isolated regions within the scope of the intended meaning. For example, electrically isolated or poorly connected regions include regions that are resistively coupled to other regions.

Methods for optically inspecting or testing indirect bandgap semiconductor devices such as photovoltaic devices and solar cells differ in the manner of excitation of the devices. In electroluminescence imaging, an external electrical signal or forward bias (voltage or current) is applied to the contact terminals of a solar cell and light emitted in response to the applied forward bias is observed and/or recorded. This method is generally applicable to completed devices. Electroluminescence images with good spatial resolution may be taken of typical industrial solar cells in about 1 second using commercially available CCD cameras.

In photoluminescence imaging, a semiconductor wafer or a completed solar cell is excited by external illumination suitable to induce photoluminescence and the emitted light is observed and/or recorded.

Figure 1:
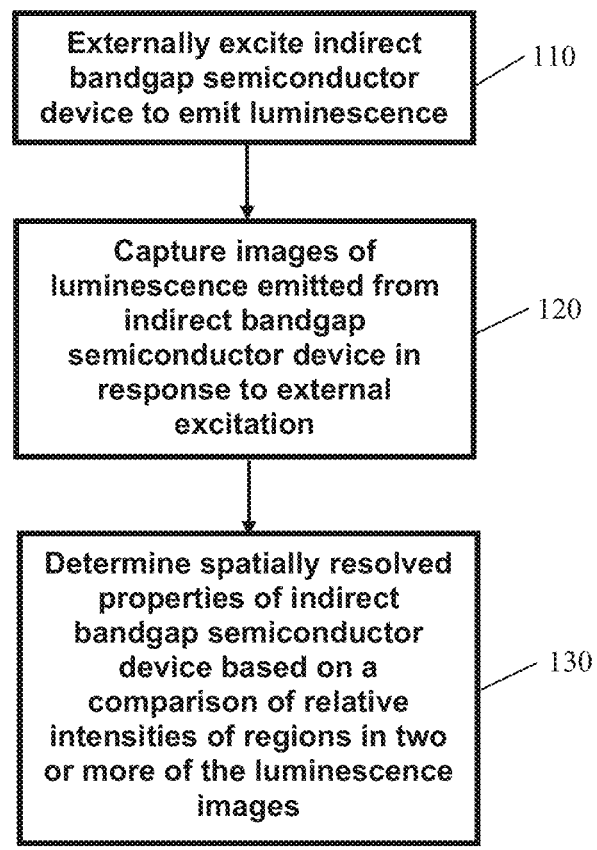
FIG. 1 is a flow diagram of a method for determining spatially resolved properties of an indirect bandgap semiconductor device in accordance with an embodiment of the present invention.

FIG. 1 is a flow diagram of a method for determining spatially resolved properties of an indirect bandgap semiconductor device. Such spatially resolved properties include, for example, electrically isolated and poorly connected regions of the indirect bandgap semiconductor device.

Referring to FIG. 1, the indirect bandgap semiconductor device is externally excited to emit luminescence at step 110. Such external excitation may comprise illumination of the indirect bandgap semiconductor device with light suitable to induce emission of photoluminescence and/or application of an electrical signal (e.g., a voltage or current) to contact terminals of the indirect bandgap semiconductor device to induce emission of electroluminescence. The voltage level across the contact terminals of the indirect bandgap semiconductor device may be varied relative to an open circuit value (generated in response to the illumination) while illuminating the indirect bandgap semiconductor device to obtain different or more useful photoluminescence images, in certain cases. The voltage across contact terminals of the indirect bandgap semiconductor device can be varied relative to an open circuit value, for example, by applying any of an external bias, a load, a short circuit or a voltage to the contact terminals of the indirect bandgap semiconductor device. Alternatively, current may be injected into or extracted out of the contact terminals of the indirect bandgap semiconductor device.

At step 120, images of luminescence emitted by the indirect bandgap semiconductor device in response to the external excitation are captured. Such images may comprise any of the following:

an electroluminescence image generated by exciting the indirect bandgap semiconductor device with an electrical signal;

a photoluminescence image generated by exciting the indirect bandgap semiconductor device with incident light suitable for inducing photoluminescence whilst contact terminals of the indirect bandgap semiconductor device are maintained in an open circuit state; and a photoluminescence image generated by exciting the indirect bandgap semiconductor device with incident light suitable for inducing photoluminescence and simultaneously varying a voltage level across contact terminals of the indirect bandgap semiconductor device relative to an open circuit value.

At step 130, the luminescence images are processed to determine spatially resolved properties of the indirect bandgap semiconductor device based on a comparison of relative intensities of regions in two or more of the luminescence images. The spatially resolved properties may be determined by comparing a ratio of intensities between different regions in one of the luminescence images with a ratio of intensities between corresponding regions in one or more of the other luminescence images.

Comparing Relative Intensities of Regions in Luminescence Images

In one embodiment of the method of FIG. 1, a comparison of relative intensities of regions is made between:

(i) an electroluminescence image generated by application of an electrical excitation signal across contact terminals of the indirect bandgap semiconductor device; and (ii) a photoluminescence image generated with the contact terminals of the indirect bandgap semiconductor device in an open circuit condition.

Regions that are of lower relative intensity in the electroluminescence image (i.e., darker relative to other regions in the electroluminescence image) but that do not exhibit any variation in intensity in the photoluminescence image are indicative of electrically isolated or poorly connected regions.

In another embodiment of the method of FIG. 1, a comparison of relative intensities of regions is made between:

(i) a photoluminescence image generated with a reduced voltage level across contact terminals of the indirect bandgap semiconductor device relative to an open circuit value; and (ii) a photoluminescence image generated with the contact terminals of the indirect bandgap semiconductor device in an open circuit condition.

Regions that are of higher relative intensity in the reduced voltage level photoluminescence image (i.e., lighter relative to other regions in the electroluminescence image) but that do not exhibit any variation in intensity in the open circuit photoluminescence image are indicative of electrically isolated or poorly connected regions.

In a further embodiment of the method of FIG. 1, a comparison of relative intensities of regions is made between:

(i) an electroluminescence image generated by application of an electrical excitation signal across contact terminals of the indirect bandgap semiconductor device; and (ii) a photoluminescence image generated with a reduced voltage level across contact terminals of the indirect bandgap semiconductor device relative to an open circuit value.

Regions that are of lower relative intensity in the electroluminescence image (i.e., darker relative to other regions in the electroluminescence image) and that are of higher relative intensity in the photoluminescence image are indicative of electrically isolated or poorly connected regions.

In a still further embodiment of the method of FIG. 1, a comparison of relative intensities of regions is made between:

(i) a first electroluminescence image generated by application of a first level of electrical excitation signal across contact terminals of the indirect bandgap semiconductor device; and (ii) a second electroluminescence image generated by application of a second level of electrical excitation signal across contact terminals of the indirect bandgap semiconductor device.

The first level of electrical excitation signal is higher than the second level of electrical excitation signal (e.g., a first voltage higher than a second voltage). Regions that are of lower relative intensity in the first electroluminescence image (i.e., darker relative to other regions in the electroluminescence image) but that are not of lower relative intensity in the second electroluminescence image are indicative of electrically isolated or poorly connected regions. In alternative embodiments, a comparison of relative intensities of regions may be made between more than 2 electroluminescence images.

Examples Using Electroluminescence and Photoluminescence Images

Figure 2A:
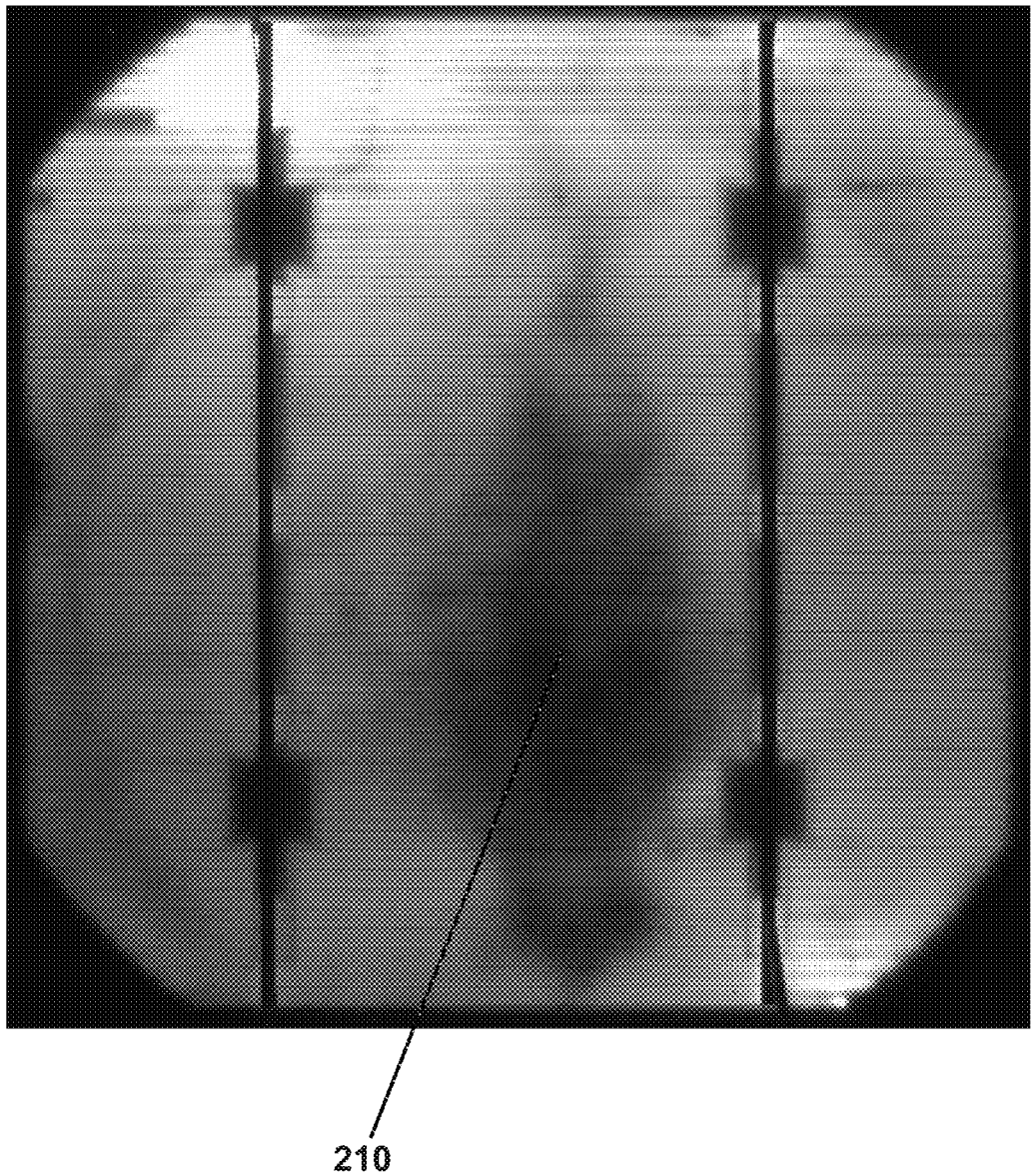
FIGS. 2a, 2b and 2c are luminescence images of an imperfect solar cell.
Figure 2B:
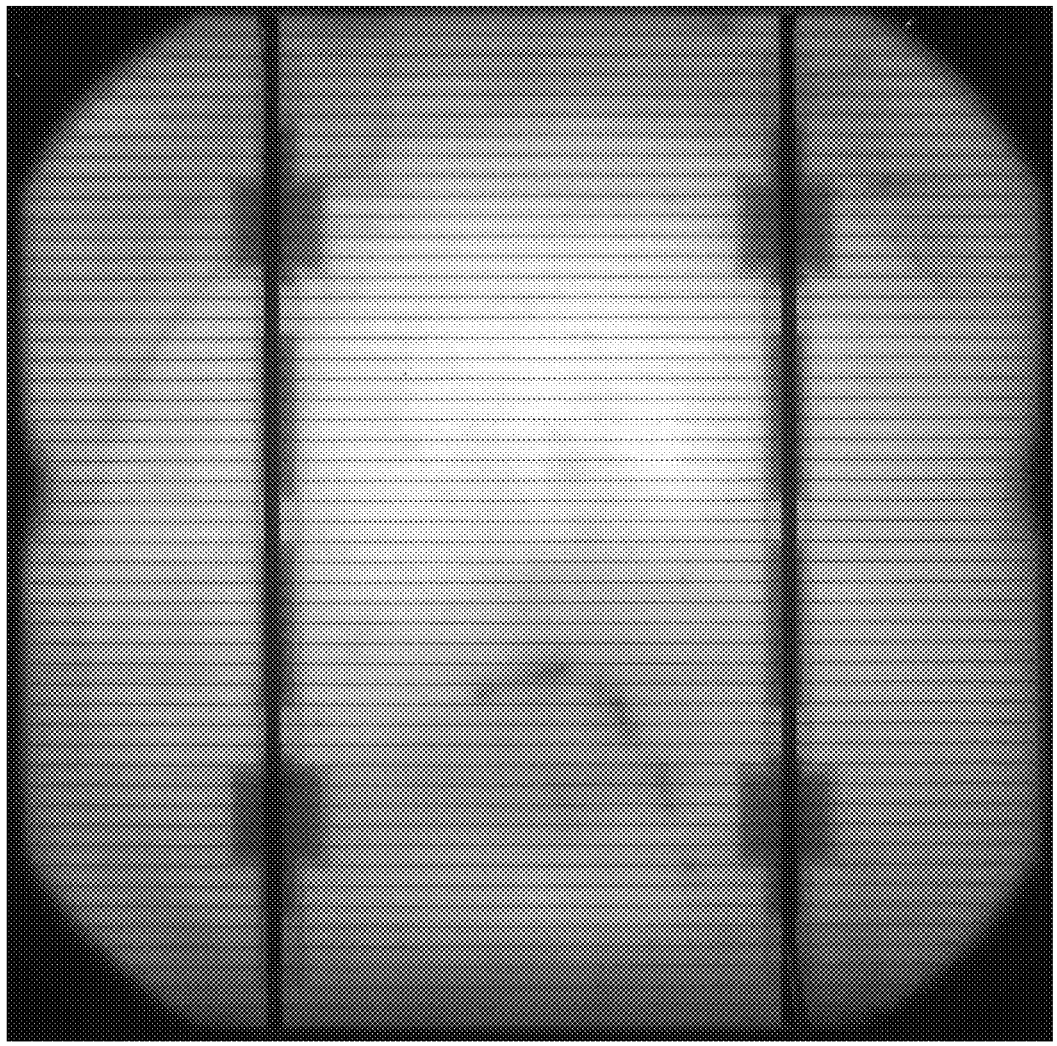
Figure 2C:
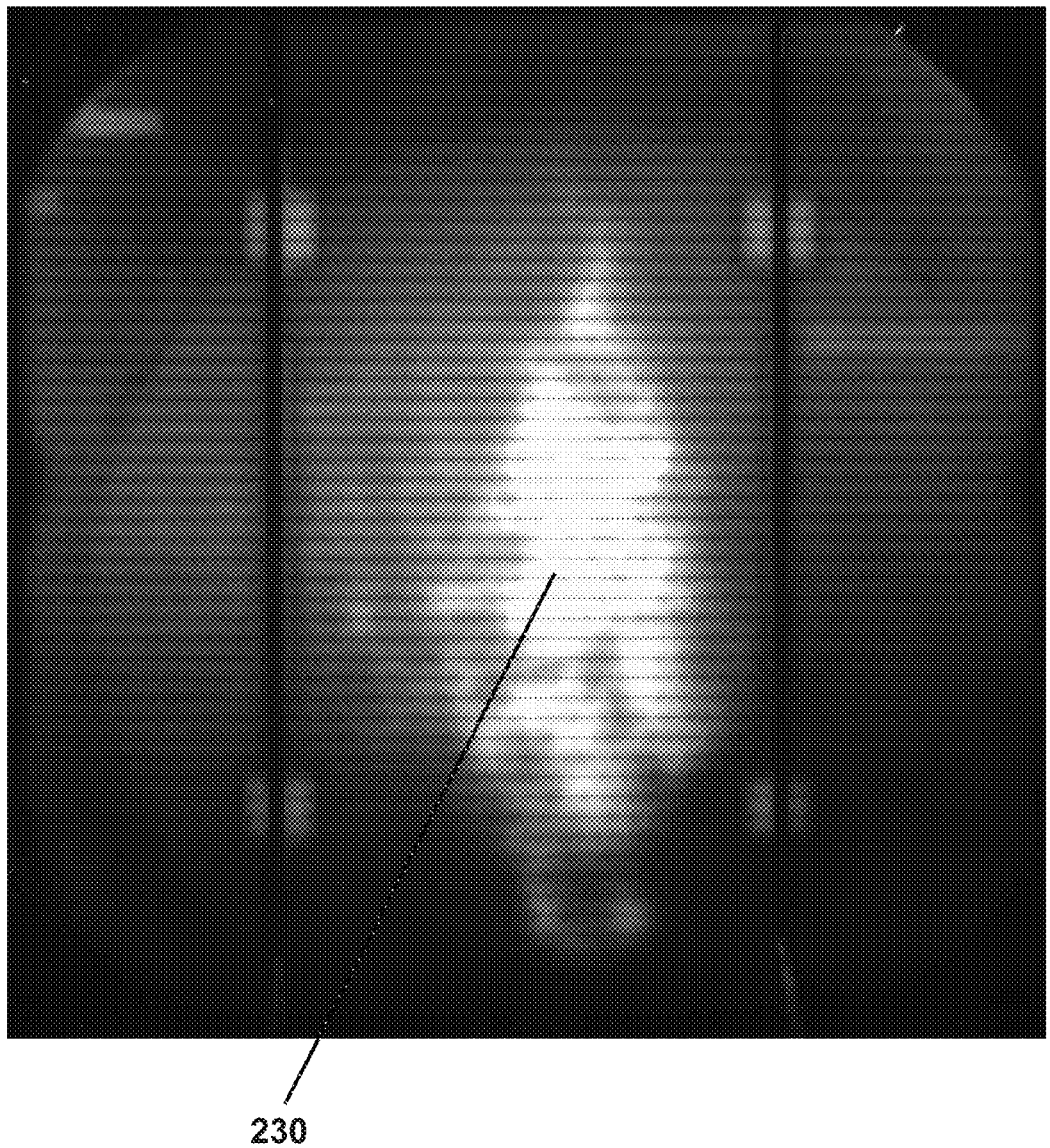

FIGS. 2a to 2c are real examples of electroluminescence and photoluminescence images generated of an imperfect solar cell. The images show two bus bars disposed vertically (i.e., from top to bottom of the image) and multiple thin fingers disposed horizontally across the bus bars (i.e., from left to right across the image).

FIG. 2a shows an electroluminescence image of an imperfect solar cell. The image was obtained by applying an electrical excitation signal across the contact terminals of the solar cell and capturing or recording the electroluminescence emitted from the solar cell in response to the electrical excitation signal. The electrical excitation signal was of 25 mA/cm$^2$ current density.

The relatively darker region 210 in the centre of the image of FIG. 2a is a region of relatively lower intensity compared to other adjacent regions in the image. The region 210 may be due to either:

a defect in the semiconductor substrate material (e.g., contamination), which would likely result in a reduced lifetime of the solar cell, or an electrically isolated region in the solar cell structure, in which relatively less current is flowing compared to regions of relatively higher intensity.

FIG. 2b shows a photoluminescence image of the same imperfect solar cell that is the subject of FIG. 2a. The image of FIG. 2b was obtained by illuminating the solar cell with illumination equivalent to about one Sun, whilst maintaining an open circuit across the solar cell's contact terminals, and capturing or recording the photoluminescence emitted from the solar cell in response to the illumination.

No relatively darker or lighter regions of significance are visible in the image of FIG. 2b in those regions 210 that appear relatively dark in the electroluminescence image of FIG. 2a.

FIG. 2c shows a photoluminescence image of the same imperfect solar cell that is the subject of FIGS. 2a and 2b. The image of FIG. 2c was obtained by illuminating the solar cell with light suitable for inducing photoluminescence, simultaneously applying a short circuit across the contact terminals of the solar cell, and capturing or recording the photoluminescence emitted from the solar cell in response to the illumination. The electrical excitation signal was of 25 mA/cm$^2$ current density. The effect of the short circuit is to lower the voltage level across the contact terminals of the solar cell, relative to an open circuit value. As a result, carriers generated in response to the illumination are extracted from the solar cell, thus resulting in a darker image of the solar cell. It should be noted that other load conditions, external voltages or external currents may alternatively be applied to the contact terminals of the solar cell in place of a short circuit to achieve the same or a similar effect.

A relatively lighter region 230 (i.e., a region of relatively higher intensity) is observable in the centre of the image of FIG. 2c. The region 230 of higher luminescence intensity compared to other regions may be due to either:
  an enhanced lifetime of the solar cell, or
  an electrically isolated region in the solar cell structure, in which relatively less current is flowing compared to regions of relatively lower intensity.

As described above, the regions of relatively lower intensity 210 and relatively higher intensity 230 in the central region of FIGS. 2a and 2c, respectively, indicate either:
  a variation in the material quality (i.e. of the local minority carrier lifetime), or
  an electrically isolated region in the solar cell structure, in which relatively less current is flowing compared to regions of relatively lower intensity.

Thus, when either the electroluminescence image of FIG. 2a or the photoluminescence image of FIG. 2c is considered alone, the respective image fails to provide sufficiently conclusive information about the cause of the regions of relatively lower intensity 210 and relatively higher intensity 230 in the central region of FIGS. 2a and 2c, respectively.

However, when the electroluminescence image of FIG. 2a is compared with the photoluminescence image of either FIG. 2b or FIG. 2c, the cause of the region of relatively lower or higher intensity can be determined. The cause of a region of relatively lower or higher intensity can also be determined by comparison of the photoluminescence images of FIG. 2b and FIG. 2c.

With reference to the photoluminescence image of FIG. 2b, the absence of a region of relatively lower intensity in the centre indicates that the semiconductor material in the central region of the solar cell is not degraded. Thus, a comparison of FIG. 2b with either FIG. 2a or FIG. 2c indicates that the region of relatively lower or relatively higher intensity in the centre, respectively, is indicative of an electrically isolated or partially connected region in the solar cell and is not indicative of a reduced minority carrier lifetime in that region.

With reference to the electroluminescence image of FIG. 2a and the photoluminescence image of FIG. 2c, the presence of a region of lower intensity relative to other regions within that electroluminescence image and the presence of a corresponding region in the centre of relatively higher intensity in the photoluminescence image with reduced external voltage indicates that the semiconductor material in the central region of the solar cell is poorly connected or electrically isolated from the rest of the cell. Such a variation in the contrast in the two luminescence images cannot be caused by variations in the minority carrier lifetime. The reduced luminescence intensity in FIG. 2a is a result of a voltage drop over the series resistance leaving the central area at lower voltage. In FIG. 2c the region of higher luminescence intensity is also caused by a voltage drop over the series resistance, leaving the central region at a higher voltage, which is manifested as higher luminescence intensity.

Figure 3:
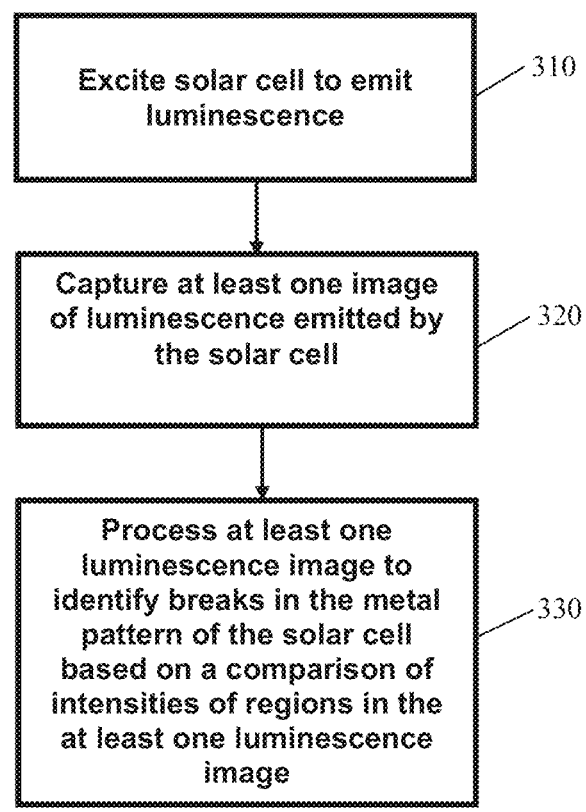
FIG. 3 is a flow diagram of a method for identifying electrically isolated or poorly connected regions in a solar cell in accordance with an embodiment of the present invention.

FIG. 3 is a flow diagram of a method for identifying electrically isolated or poorly connected regions in a solar cell that comprises a portion of indirect bandgap semiconductor wafer having at least one metal pattern disposed on a surface thereof. The metal pattern may comprise a grid comprising a plurality of fingers electrically connected to at least one bus bar. The fingers are typically, but not essentially, disposed substantially parallel to each other. The electrically isolated or poorly connected regions may comprise breaks (i.e., electrical discontinuities) in a finger, a bus bar, or in a connection between a finger and a bus bar.

Referring to FIG. 3, the solar cell is excited to emit luminescence at step 310. Such excitation may comprise:
  application of an electrical signal or forward bias (e.g., a voltage or current) to the contact terminals of the solar cell to induce emission of electroluminescence, and/or
  illumination of the solar cell with light suitable to induce emission of photoluminescence and simultaneously varying a voltage level across the contact terminals of the solar cell relative to an open circuit value while illuminating the solar cell.

The voltage across contact terminals of the solar cell may be varied relative to an open circuit value, for example, by applying any of an external bias, a load, a short circuit or a voltage to the contact terminals of the solar cell. Alternatively, current may be injected into or extracted out of the contact terminals of the solar cell.

At step 320, at least one image of luminescence emitted from the solar cell in response to the excitation is recorded or captured. Such images may comprise any of the following:
  an electroluminescence image generated by exciting the solar cell with an electrical signal or forward bias, as described hereinbefore; and
  a photoluminescence image generated by exciting the solar cell with incident light suitable for inducing photoluminescence and simultaneously varying the voltage level across the contact terminals of the solar cell relative to an open circuit value. Variation of the voltage level across the contact terminals of the solar cell relative to an open circuit value may be performed by applying an external bias, a load, a short circuit or a voltage across the contact terminals of the solar cell. Alternatively, current may be injected into or extracted from the contact terminals of the solar cell.

At step 330, the at least one luminescence image is processed to identify breaks in the metal pattern based on a comparison of intensities of regions in the at least one luminescent image. The processing step may comprise comparing a ratio of intensities between different regions in one of the luminescence images with a ratio of intensities between corresponding regions in at least one other of the luminescence images.

Breaks in the metal pattern of a solar cell may be identified based on a comparison of relative intensities of regions in one or more luminescent images. For example, a broken finger may be identified based on detection of a region of relatively lower intensity in a single electroluminescence image. Alternatively, a broken finger may be identified based on detection of a region of relatively higher intensity in a single photoluminescence image with simultaneous variation of the voltage level across the contact terminals of the solar cell relative to an open circuit value.

Such regions of relatively higher or lower intensity are typically elongated in shape and occur proximate to a portion of the broken finger.

When using two or more luminescence images to identify electrically isolated or poorly connected regions in a solar cell, the luminescence images may comprise:
- an electroluminescence image generated by exciting the solar cell with an electrical signal;
- a photoluminescence image generated by exciting the solar cell with incident light suitable for inducing photoluminescence whilst contact terminals of the solar cell are maintained in an open circuit state; and
- a photoluminescence image generated by exciting the solar cell with incident light suitable for inducing photoluminescence and simultaneously varying a voltage level across contact terminals of the solar cell relative to an open circuit value.

Figure 4A:
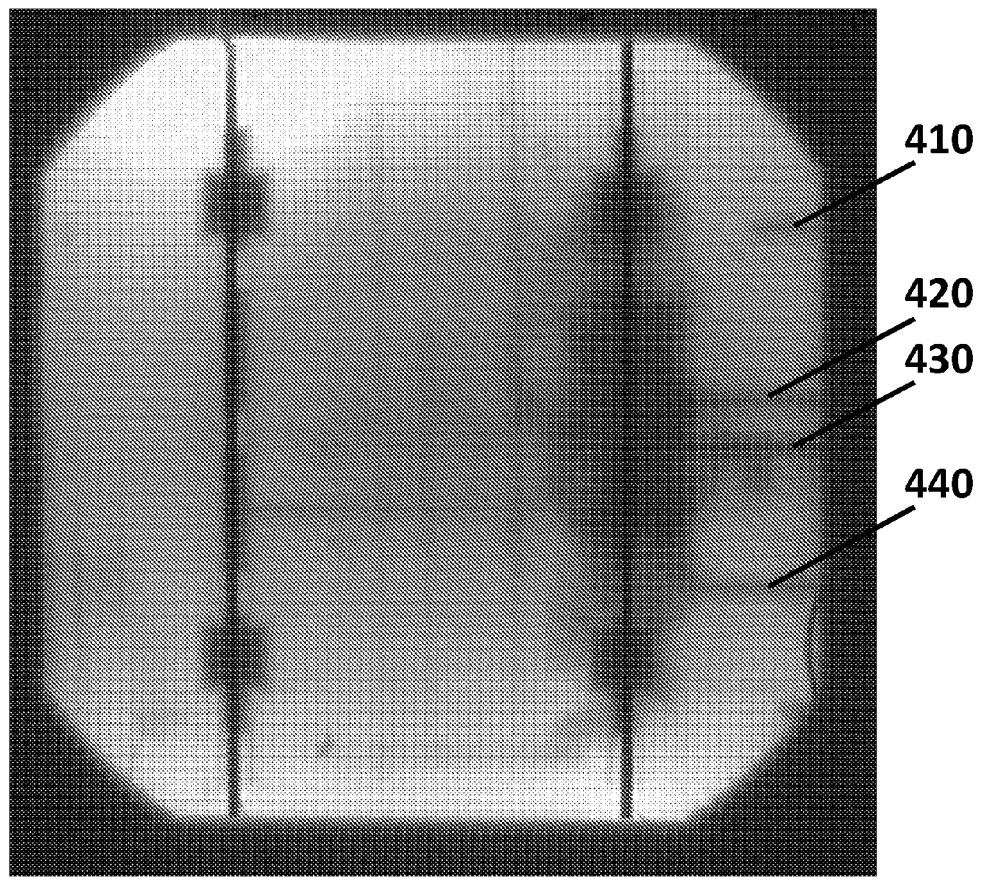
FIGS. 4a and 4b are luminescence images of an imperfect solar cell.
Figure 4B:
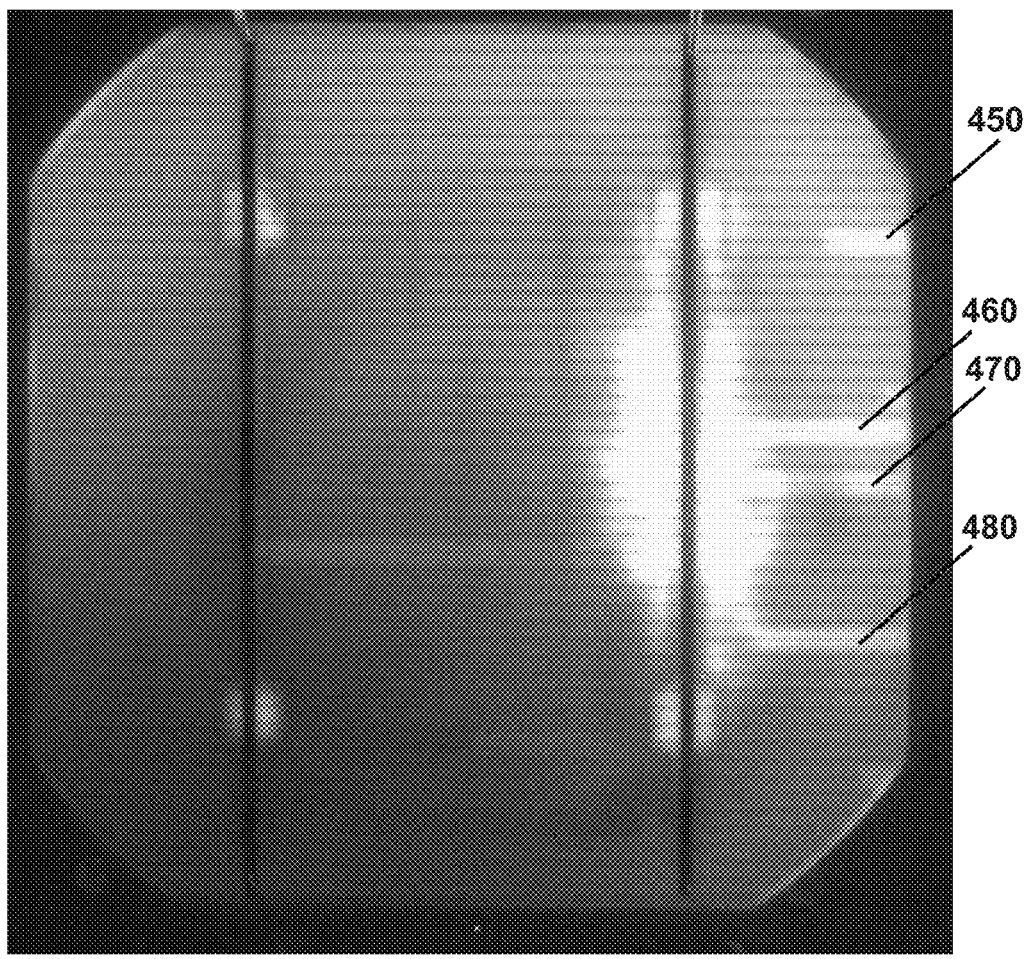

FIGS. 4a and 4b are real examples of electroluminescence and photoluminescence images generated of an imperfect solar cell. The images show two bus bars disposed vertically (i.e., from top to bottom of the image) and multiple thin fingers disposed horizontally across the bus bars (i.e., from left to right across the image).

FIG. 4a shows an image of an imperfect solar cell generated using electroluminescence imaging. The image was obtained by applying an external bias (a current density of 25 mA/cm$^2$) to the contact terminals of the solar cell and capturing or recording the electroluminescence emitted from the solar cell in response to excitation by the external bias voltage.

Inspection of FIG. 4a reveals elongated regions 410, 420, 430 and 440 of relatively lower intensity (i.e., relatively darker) that are proximate to a portion of a finger. Inspection of the same damaged solar cell under an optical microscope confirmed that the elongated regions 410, 420, 430 and 440 of relatively lower intensity (i.e., generally darker than the adjacent regions) are indicative of broken metal fingers at corresponding locations in the solar cell. A break in a finger is generally located at one end of a corresponding elongated region.

There is thus a direct correlation between regions of relatively lower intensity in an electroluminescence image of a solar cell and locations of broken metal fingers in that solar cell.

An alternative method for identifying broken metal fingers in a solar cell uses photoluminescence imaging with simultaneous varying of the voltage level across the contact terminals of the solar cell, relative to an open circuit value. The effect of a broken metal finger is to electrically isolate (partially or fully) a region proximate to the broken metal finger from the remainder of the solar cell. Decreasing the voltage level across the contact terminals of the solar cell, relative to an open circuit value, results in a sharp drop in the voltage across all regions of the solar cell that are well connected electrically. Regions that are poorly electrically connected to the remainder of the solar cell, such as broken metal fingers, are manifested as regions of relatively higher intensity (i.e., lighter regions) in a photoluminescence image.

FIG. 4b shows an image of the imperfect solar cell that is the subject of FIG. 4a, which was generated using photoluminescence imaging together with decreasing the voltage level across the contact terminals of the solar cell, relative to an open circuit value. More specifically, a short circuit was applied across the contact terminals of the solar cell while the solar cell was illuminated with illumination equivalent to about one Sun). The effect of the short circuit is that carriers generated as a result of illumination of the solar cell are extracted from the solar cell. Carrier extraction results in a darker image of the solar cell. Thus, the elongated regions 450, 460, 470 and 480 of relatively higher intensity (i.e., generally lighter than the adjacent regions) proximate to finger portions in FIG. 4b are indicative of lower levels of carrier extraction from the solar cell. Inspection of the same damaged solar cell under an optical microscope confirmed that the elongated regions 450, 460, 470 and 480 of relatively higher intensity are indicative of broken metal fingers at corresponding locations in the solar cell. A break in a finger is generally located at one end of a corresponding elongated region.

There is thus a direct correlation between regions of relatively higher intensity in a photoluminescence image of a solar cell and locations of broken metal fingers in that solar cell.

Figure 5:
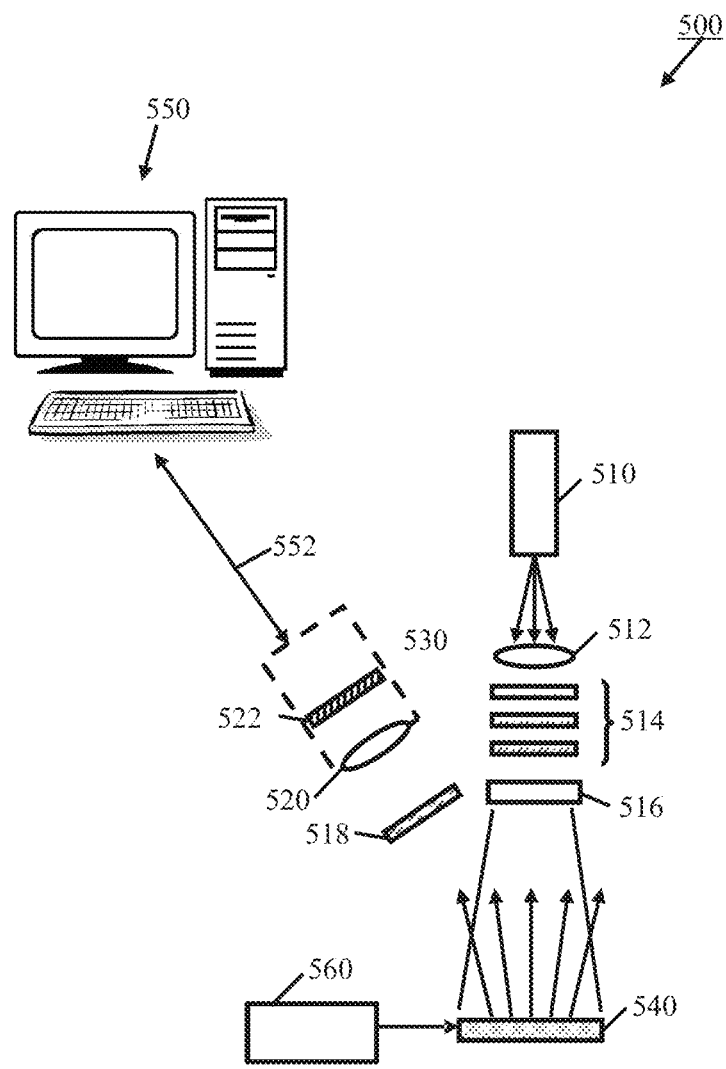
FIG. 5 is a block diagram of an apparatus for determining spatially resolved properties of an indirect bandgap semiconductor device such as a solar cell in accordance with an embodiment of the present invention.

FIG. 5 is a block diagram of an apparatus 500 for identifying or determining spatially resolved properties in indirect bandgap semiconductor devices such as solar cells.

The apparatus 500 comprises a light source 510, an optional short-pass filter unit 514, an image capture device 522 and bias means 560. The short-pass filter unit 514 may comprise one or more short pass filter/s. A short pass filter passes through the excitation light and absorbs or reflects an unwanted long wavelength emission(s). Examples of short pass filters include coloured filters and dielectric interference filters. Alternatively, a dielectric mirror may be used (e.g. under 45 degrees) that reflects that part of the light that is to be used and transmits the unwanted long wavelength light. The short pass filter unit may also comprise a combination of short pass filters and dielectric mirrors. The apparatus may also comprise a collimator 512 and/or a homogenizer 516, which is a device for converting a collimated beam of light that has non-uniform intensity into a uniformly illuminated region of a plane perpendicularly incident to the collimated beam. Examples include cross cylindrical lens array(s) and a micro lens array. A collimator may be lenses of various sorts.

Photoluminescence imaging may be performed whilst varying the voltage across the contact terminals of the indirect bandgap semiconductor device 540 relative to an open circuit voltage (generated by the photoluminescence) using the apparatus 500 of FIG. 5. A voltage varying means 560 is coupled to the indirect bandgap semiconductor device 540 for varying the voltage across the contact terminals of the indirect bandgap semiconductor device 540 relative to an open circuit voltage. The voltage varying means may comprise an external bias means, a voltage source, a current source, a current sink, a load, a short circuit, or any other suitable voltage varying means known in the electrical engineering arts. Reduction of the voltage across the electrical contacts of indirect bandgap semiconductor device 540 relative to an open circuit voltage causes carriers, which would otherwise have recombined within the indirect bandgap semiconductor device 540 under open circuit conditions to be extracted from the indirect bandgap semiconductor device 540 through the electrical contacts of the indirect bandgap semiconductor device 540 to a point of lower potential. The result of such carrier extraction is a reduction of luminescence by the indirect bandgap semiconductor device 540. The number of carriers extracted, and thus the level of luminescence generated by the indirect bandgap semiconductor device 540, depends on the amount of variation of the voltage level across the contact terminals of the indirect bandgap semiconductor device 540 relative to an open circuit value.

In the embodiment of FIG. 5, the elements of the apparatus 500 are arranged as follows: a light source 510 facing the indirect bandgap semiconductor device 540, the collimator 512, the short-pass filter unit 514, and the homogenizer 516 optically aligned in that sequence. In another embodiment, the ordering of the collimator 512 and the short-pass filter unit 514 may be reversed. A field lens (not shown) may be used between the homogenizer and the indirect bandgap semiconductor device 540. The elements are spaced apart from the indirect bandgap semiconductor device 540 so that a large area of the indirect bandgap semiconductor device 540 can be illuminated.

The light source 510 generates light suitable for inducing photoluminescence in the indirect bandgap semiconductor device 540. The total optical power of the generated light may exceed 1.0 Watt. Light sources of higher power are able to more quickly and intensely induce photoluminescence in the indirect bandgap semiconductor device 540. The light source 510 may generate monochromatic or substantially monochromatic light. The light source 510 may be at least one laser. For example, an 808 nm diode laser may be used to generate monochromatic light. Two or more lasers with different principal wavelengths may also be practiced. Another light source 510 may comprise a broad spectrum light source (e.g., a flash lamp) combined with suitable filtering to provide partly filtered light. Still another light source 510 may be a high-powered light emitting diode (LED). Yet another light source 510 may comprise an array of light emitting diodes (LED). For example, such an LED array may comprise a large number (e.g. 60) LEDs in a compact array with heatsinking. Other high powered light sources may be practiced without departing from the scope and spirit of the invention.

The light from the light source 510 is collimated into parallel beams by a collimator or collimator unit 512, which may comprise more than one element. Short-pass filtering is applied to the generated light. This may be done using an interference short-pass filter unit 514 comprising one or more filter elements. Short-pass filtering the generated light reduces long-wavelength light above a specified emission peak. The short-pass filter 514 may reduce by a factor of about 10 or more the total photon flux in a long-wavelength tail of the generated light. The long-wavelength tail may begin at a wavelength that is about ten percent (10%) higher than a longest wavelength emission peak of the light source 510. For example, the filtering may remove unwanted spectrum components such as infra-red components with wavelengths in the range of 900 nm to 1800 nm or a sub-range of that range. Multiple short-pass filters may be used because one filter may not be sufficient itself to remove or reduce unwanted spectrum components. The short-pass filters may be implemented at numerous different positions in the overall combination of optical elements between the light source 510 and the indirect bandgap semiconductor device 540. If more than one short pass filter is used, then one or more of the filters may be arranged so that they are tilted under some angle against the optical axis of the collimated beam to avoid multiple reflections of the reflected light. The short-pass filtered and collimated light may then be homogenized by a homogenizer 516 to homogeneously illuminate a large area of the indirect bandgap semiconductor device 540. However the ordering of the steps may be altered. The illuminated area of the indirect bandgap semiconductor device 540 may be greater than or equal to about 1.0 cm$^2$. The homogenizer 516 distributes the collimated beams evenly across the surface of the indirect bandgap semiconductor device 540.

The illumination incident on the surface of the indirect bandgap semiconductor device 540 is sufficient to induce photoluminescence in the indirect bandgap semiconductor device 540. This photoluminescence is represented in FIG. 5 by arrows or rays emanating from a planar surface of the indirect bandgap semiconductor device 540. The external photoluminescence quantum efficiency of silicon can be very low (of the order of <10$^{-6}$). An image capture device 530 captures images of the photoluminescence induced in the indirect bandgap semiconductor device 540. The short pass filter unit 514 reduces or removes incident light from the light source 510 from being received by an image capture device 530. Light source tail radiation may be of the order of 10$^{-4}$ of a source peak, which can significantly exceed the photoluminescence efficiency of silicon (of the order of 10$^{-6}$) in contrast to that of direct bandgap semiconductors like AlGaAs (of the order of 10$^{-2}$). An optional long pass filter unit 518 may be used in combination with the image capture device 530 in order to block reflected excitation light to contribute to the measured signal.

The image capture device 530 comprises a focusing element 520 (e.g. one or more lenses) and a focal plane array 522 of light sensitive electronic elements. In this embodiment, the focal plane array 522 of light sensitive electronic elements comprises an array of charge coupled devices (CCD). The focal plane array may be made of silicon and may be cooled. Cooling improves the signal-to-noise ratio of such a focal plane array. For example, the image capture device 530 may be a digital video camera having a silicon CCD array and be provided with a digital interface (e.g., USB or Firewire) or storage media (e.g., a DV tape or memory stick) for communication of recorded images. Alternatively, the focal plane array 522 of light sensitive electronic elements may be made from InGaAs.

Image processing techniques may be applied to the photoluminescence images to quantify specified electronic properties of the indirect bandgap semiconductor device 540. Spatial variations of the photoluminescence intensity are checked for and identified. As shown in FIG. 5, a general-purpose computer 550 can acquire and analyze photoluminescence images recorded by the image capture device 530 via a communications channel 552, which may include a suitable communications interface and/or storage device. The image processing techniques may be implemented in software, hardware, or a combination of the two. Imaging is distinct from photoluminescence mapping, which is slow and therefore not suitable for industrial application as an inline production testing tool, and spectroscopic testing of photoluminescence, which typically involves testing a small area of a semiconductor. The system in accordance with this embodiment of the invention can be used to identify defective areas of the indirect bandgap semiconductor device 540.

Electroluminescence imaging may be performed by applying a forward bias (i.e., voltage or current) across the contact terminals of the indirect bandgap semiconductor device 540 using the voltage varying means 560 or another suitable forward bias generating means known in the electrical arts. Electroluminescence images may be captured using the image capture device 530 and processed using the general-purpose computer 550, in a similar manner to that described hereinbefore with reference to photoluminescence imaging. However, the light source 510, collimator 512, interference short-pass filter 514 and homogenizer 516 are not used in the case of electroluminescence imaging.

The foregoing description provides exemplary embodiments only, and is not intended to limit the scope, applicability or configurations of the present invention. Rather, the description of the exemplary embodiments provides those skilled in the art with enabling descriptions for implementing an embodiment of the invention. Various changes may be made in the function and arrangement of elements without departing from the spirit and scope of the invention as set forth in the claims hereinafter.

Where specific features, elements and steps referred to herein have known equivalents in the art to which the invention relates, such known equivalents are deemed to be incorporated herein as if individually set forth. Furthermore, features, elements and steps referred to in respect of particular embodiments may optionally form part of any of the other embodiments unless stated to the contrary.

The term "comprising", as used herein, is intended to have an open-ended, non-exclusive meaning. For example, the term is intended to mean: "including principally, but not necessarily solely" and not to mean "consisting essentially of" or "consisting only of". Variations of the term "comprising", such as "comprise", "comprises" and "is comprised of", have corresponding meanings.

The invention claimed is:

1. A method for identifying electrically isolated or poorly connected regions in a solar cell, said solar cell comprising a portion of an indirect bandgap semiconductor wafer having at least one metal pattern disposed on a surface thereof, said method comprising the steps of:
   exciting said solar cell to emit luminescence;
   capturing at least one image of said emitted luminescence; and
   identifying electrically isolated or poorly connected regions in said solar cell based on a comparison of intensities of regions in said at least one luminescence image.

2. A method according to claim 1, wherein said step of exciting said solar cell to emit luminescence comprises the step of exciting said solar cell with an electrical signal to induce emission of electroluminescence.

3. A method according to claim 2, wherein an electrically isolated or poorly connected region in said solar cell is identified based on detection of a region of relatively lower luminescence intensity.

4. A method according to claim 1, wherein said step of exciting said solar cell to emit luminescence comprises the sub-steps of:
   illuminating said solar cell with incident light suitable for inducing photoluminescence; and
   simultaneously varying a voltage level across contact terminals of said solar cell relative to an open circuit value.

5. A method according to claim 4, wherein said sub-step of simultaneously varying a voltage level across contact terminals of said solar cell comprises a step selected from the group consisting of:
   applying an external bias across contact terminals of said solar cell;
   applying a load across contact terminals of said solar cell;
   applying a short circuit across contact terminals of said solar cell;
   applying a voltage across contact terminals of said solar cell;
   injecting current into contact terminals of said solar cell; and
   extracting current from contact terminals of said solar cell.

6. A method according to claim 4, wherein an electrically isolated or poorly connected region in said solar cell is identified based on detection of a region of relatively higher luminescence intensity.

7. A method according to claim 1, wherein said step of identifying electrically isolated or poorly connected regions in said solar cell comprises comparing relative intensities of regions in at least two luminescence images, the luminescence in said at least two luminescence images being emitted from said solar cell in response to different excitation conditions.

8. A method according to claim 7, wherein said at least two luminescence images are selected from the group consisting of:
   an electroluminescence image generated by exciting said solar cell with an electrical signal;
   a photoluminescence image generated by exciting said solar cell with incident light suitable for inducing photoluminescence whilst contact terminals of said solar cell are maintained in an open circuit state; and
   a photoluminescence image generated by exciting said solar cell with incident light suitable for inducing photoluminescence and simultaneously varying a voltage level across contact terminals of said solar cell relative to an open circuit value.

9. An apparatus for identifying electrically isolated or poorly connected regions in a solar cell, said solar cell comprising a portion of an indirect bandgap semiconductor wafer having at least one metal pattern disposed on a surface thereof, said apparatus comprising:
   an excitation source configured for exciting said solar cell to emit luminescence;
   an image capture device configured for capturing at least one image of said emitted luminescence; and
   a computer programmed to identify electrically isolated or poorly connected regions in said solar cell based on a comparison of intensities of regions in said at least one luminescence image.

10. An apparatus according to claim 9, wherein said excitation source comprises an electrical signal source configured for applying an electrical signal to contact terminals of said solar cell to induce electroluminescence in said solar cell.

11. An apparatus according to claim 10, wherein said computer is programmed to identify an electrically isolated or poorly connected region in said solar cell based on detection of a region of relatively lower luminescence intensity.

12. An apparatus according to claim 9, wherein said excitation source comprises:
   a light source configured for illuminating said solar cell with light suitable for inducing photoluminescence in said solar cell; and
   a voltage varying source configured for varying a voltage level across contact terminals of said solar cell relative to an open circuit value.

13. An apparatus according to claim 12, wherein said voltage varying source comprises at least one of:
   an external bias means;
   a load;
   a short circuit;
   a voltage source;
   a current source; or
   a current sink.

14. An apparatus according to claim 12, wherein said computer is programmed to identify an electrically isolated or poorly connected region in said solar cell based on detection of a region of relatively higher luminescence intensity.

15. An apparatus according to claim 9, wherein said computer is programmed to identify electrically isolated or poorly connected regions in said solar cell based on a comparison of relative intensities of regions in at least two luminescence images,
wherein the luminescence in each of said at least two luminescence images is emitted from said solar cell in response to different excitation conditions.

16. An apparatus according to claim 15, wherein said at least two luminescence images are selected from the group consisting of:
an electroluminescence image generated by exciting said solar cell with an electrical signal;
a photoluminescence image generated by exciting said solar cell with incident light suitable for inducing photoluminescence whilst contact terminals of said solar cell are maintained in an open circuit state; and
a photoluminescence image generated by exciting said solar cell with incident light suitable for inducing photoluminescence and simultaneously varying a voltage level across contact terminals of said solar cell relative to an open circuit value.

* * * * *